United States Patent
Ito et al.

(10) Patent No.: US 11,371,740 B2
(45) Date of Patent: Jun. 28, 2022

(54) WARM SENSATION CALCULATION APPARATUS, WARM SENSATION CALCULATION METHOD, AIR CONDITIONER, AND PROGRAM

(71) Applicants: DENSO CORPORATION, Kariya (JP); SHINSHU UNIVERSITY, Matsumoto (JP)

(72) Inventors: Yusuke Ito, Kariya (JP); Tomonori Sakoi, Ueda (JP)

(73) Assignees: DENSO CORPORATION, Kariya (JP); SHINSHU UNIVERSITY, Matsumoto (JP)

(*) Notice: Subject to any disclaimer, the term of this patent is extended or adjusted under 35 U.S.C. 154(b) by 230 days.

(21) Appl. No.: 16/727,350

(22) Filed: Dec. 26, 2019

(65) Prior Publication Data

US 2020/0132329 A1    Apr. 30, 2020

Related U.S. Application Data

(63) Continuation of application No. PCT/JP2018/022901, filed on Jun. 15, 2018.

(30) Foreign Application Priority Data

Jul. 24, 2017    (JP) .............................. JP2017-142854

(51) Int. Cl.

| | |
|---|---|
| *F24F 11/63* | (2018.01) |
| *G05B 15/02* | (2006.01) |
| *G06F 30/20* | (2020.01) |
| *F24F 110/10* | (2018.01) |
| *G06F 119/08* | (2020.01) |

(Continued)

(52) U.S. Cl.
CPC .............. *F24F 11/63* (2018.01); *G05B 15/02* (2013.01); *G06F 30/20* (2020.01); *F24F 2110/10* (2018.01); *G06F 2119/08* (2020.01)

(58) Field of Classification Search
CPC .... F24F 11/63; F24F 2110/10; F24F 2120/00; F24F 11/62; G06F 30/20; G06F 2119/08; G05B 15/02; A61B 5/026; A61B 5/16; A61B 10/00; G01D 21/00
See application file for complete search history.

(56) References Cited

U.S. PATENT DOCUMENTS

| | | | |
|---|---|---|---|
| 10,583,709 B2 * | 3/2020 | Chen ................. | B60H 1/00742 |
| 2004/0133406 A1 * | 7/2004 | Ozeki ..................... | G01W 1/17 |
| | | | 703/2 |
| 2016/0320081 A1 * | 11/2016 | Nikovski ............... | G06N 20/00 |

FOREIGN PATENT DOCUMENTS

| | | |
|---|---|---|
| JP | H04224414 A | 8/1992 |
| JP | H10278539 A | 10/1998 |

(Continued)

*Primary Examiner* — Thomas C Lee
*Assistant Examiner* — Anzuman Sharmin
(74) *Attorney, Agent, or Firm* — Harness, Dickey & Pierce, P.L.C.

(57) ABSTRACT

A warmth calculation apparatus capable of indicating warmth during a transition is provided. This warmth calculation apparatus includes: a calculator that, on the basis of a human body heat model simulating a human body, calculates a basic index indicating the warm sensation of parts of the human body under inputted environmental conditions; and a corrector that corrects the basic index utilizing, as a correction element, a heat transfer amount caused by blood flow of the human body heat model.

5 Claims, 4 Drawing Sheets

(51) Int. Cl.
*F24F 120/00* (2018.01)
*A61B 5/026* (2006.01)
*A61B 5/16* (2006.01)
*F24F 11/62* (2018.01)
*G01D 21/00* (2006.01)

(56) References Cited

FOREIGN PATENT DOCUMENTS

| | | | |
|---|---|---|---|
| JP | 2009-187050 | A | 8/2009 |
| JP | 2013096644 | A | 5/2013 |
| JP | 2014228172 | A | 12/2014 |
| JP | 6618450 | B2 * | 12/2019 |

* cited by examiner

WARM SENSATION CALCULATION APPARATUS, WARM SENSATION CALCULATION METHOD, AIR CONDITIONER, AND PROGRAM

CROSS REFERENCE TO RELATED APPLICATION

The present application is a continuation application of International Patent Application No. PCT/JP2018/022901 filed on Jun. 15, 2018, which designated the U.S. and claims the benefit of priority from Japanese Patent Application No. 2017-142854 filed on Jul. 24, 2017. The entire disclosures of all of the above applications are incorporated herein by reference.

TECHNICAL FIELD

The present disclosure relates to a warm sensation calculation apparatus, a warm sensation calculation method, an air conditioner, and a program.

BACKGROUND

A standard new effective temperature (SET*) as one of indexes indicating human warm sensation or human warm-heat sensation has been proposed.

SUMMARY

According to one example, a basic index indicating a warm sensation is calculated based on a human body heat model, and is corrected.

BRIEF DESCRIPTION OF DRAWINGS

The objects, features and advantages of the present disclosure will be more clearly understood from the following detailed description with reference to the accompanying drawings. In the accompanying drawings.

DETAILED DESCRIPTION

Figure 1:
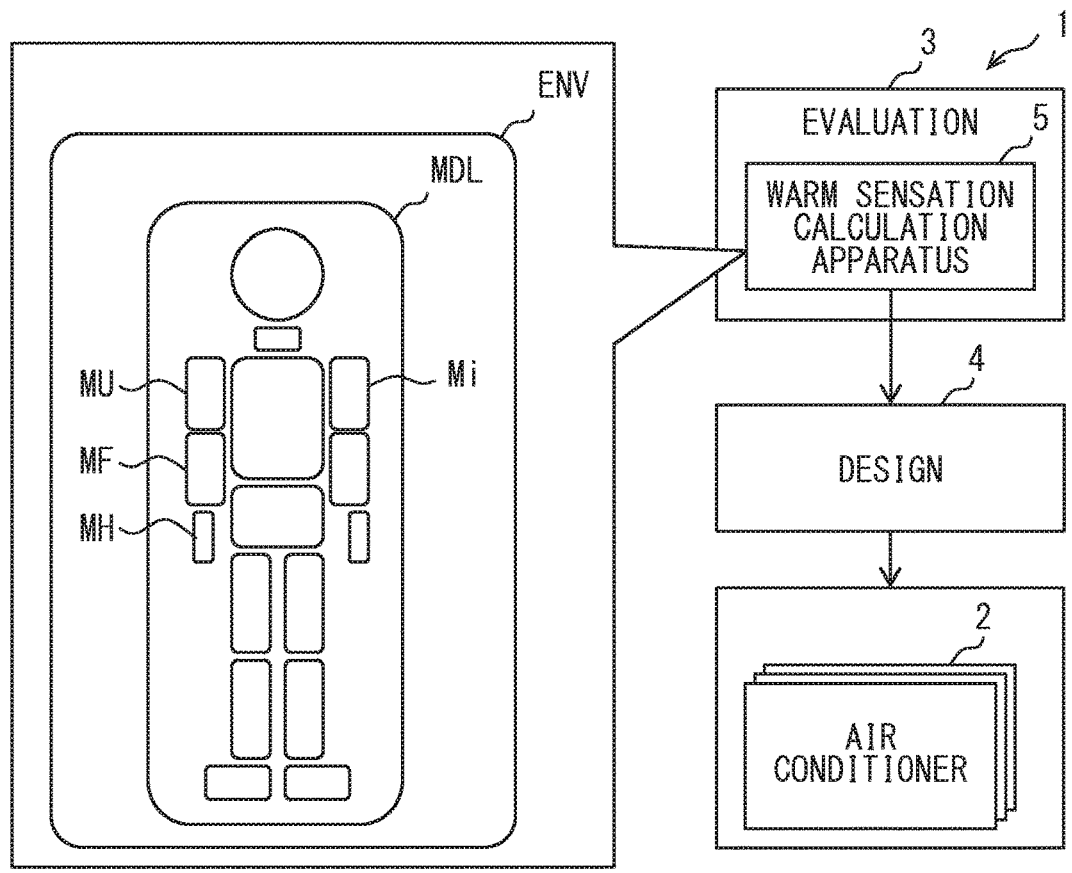
FIG. 1 is a block diagram of an air conditioner design method according to a first embodiment.

Accuracy is reduced when a relation between an environment and an object person is transitional. For example, when the environment changes transiently or when the object person enters or exits the adjusted environment, it may not be possible to correctly represent warm sensation as a whole of a human body and warm sensation as a part of the human body. In view of the above, or other aspects not mentioned, improvements for a warm sensation calculation apparatus, a warm sensation calculation method, an air conditioner, and a program are further required.

One example provides a warm sensation calculation apparatus, a warm sensation calculation method, an air conditioner, and a program capable of representing warm sensation as a whole of a human body and warm sensation as a part of the human body during a transition.

Another example provides an air conditioner capable of reflecting warm sensation as a whole of a human body and warm sensation as a part of the human body during a transition in air conditioning.

According to one example embodiment, a warm sensation calculation apparatus includes a calculator that calculates a basic index indicating warm sensation of a part of a human body and a corrector that collects the basic index by utilizing, as a correction element, a heat transfer amount due to a blood flow of a human body heat model. The corrector corrects the basic index based on the heat transfer amount so as to reflect heat inflow and heat outflow at a transition. The corrector further corrects the basic index by utilizing, as a correction element, a whole body heat storage amount (Sb) and an average body temperature (Tb) due to heat storage of the human body heat model (MDL). The corrector corrects the basic index based on the whole body heat storage amount and the average body temperature so as to reflect the heat storage of the human body at the transition. The correction element adds a direct correction component to the basic index to increase a degree of coincidence between the basic index and the warm sensation. The direct correction component corresponds to a linear function of the correction element. According to the warm sensation calculation apparatus, not only the basic index and also the correction element are reflected. Particularly, the heat transfer amount due to the blood flow of the human body heat model corresponds to the correction element. Therefore, it may be possible to represent the warm sensation of the part of the human body at the transition.

According to another example embodiment, a warm sensation calculation apparatus includes a calculator that calculates a basic index indicating warm sensation of a human and a corrector that collects the basic index by utilizing, as a correction element, a whole body heat storage amount and/or an average body temperature due to heat storage of a human body heat model. The corrector corrects the basic index based on the heat transfer amount (Qbi) due to the blood flow of the human body heat model (MDL) so as to reflect heat inflow and heat outflow at a transition. The corrector corrects the basic index based on the whole body heat storage amount and the average body temperature so as to reflect the heat storage of a human body at the transition. The correction element adds a direct correction component to the basic index to increase a degree of coincidence between the basic index and the warm sensation. The direct correction component corresponds to a linear function of the correction element. According to the warm sensation calculation apparatus, not only the basic index and also the correction element are reflected. Particularly, the whole body heat storage amount due to the heat storage of the human body heat model and/or the average body temperature correspond to the correction element. Therefore, it may be possible to represent the human warm sensation at the transition.

Furthermore, according to another example embodiment, an air conditioner includes a warm sensation calculation apparatus, an air conditioning controller that controls air conditioning in accordance with the warm sensation calculation apparatus. According to the air conditioner, the air conditioning is controlled based on the index obtained by reflecting not only the basic index but also the correction element. Therefore, it may be possible to reflect the warm sensation of the human at the transition in the air conditioning.

Furthermore, according to another example embodiment, a warm sensation calculation method includes a calculation step that calculates a basic index indicating a warm sensation of a whole of a human body or a warm sensation of a part of the human body, and a correction step that corrects the basic index by utilizing, as a correction element, a heat transfer amount due to a blood flow of a human body heat model, a whole body heat storage amount due to heat storage of a human body, and/or an average body temperature. According to the warm sensation calculation method, not only the basic index and also the correction element are reflected. Particularly, the heat transfer amount due to the blood flow of the human body heat model, the whole body heat storage amount due to the heat storage of the human body heat model, and the average blood temperature due to the heat storage of the human body heat model correspond to the correction element. Therefore, it may be possible to represent the warm sensation of the whole of the human body or the warm sensation of the part of the human body at the transition.

Furthermore, according to another example embodiment, a program causes a computer to execute the calculation step and the correction step. According to the program, not only the basic index and also the correction element are reflected. Particularly, the heat transfer amount due to the blood flow of the human body heat model, the whole heat storage amount due to the heat storage of the human body heat model, and the average blood temperature due to the heat storage of the human body heat model correspond to the correction element. Therefore, it may be possible to represent the warm sensation of the whole of the human body or the warm sensation of the part of the human body at the transition.

Hereinafter, embodiments for implementing the present disclosure will be described with reference to drawings.

First Embodiment

In FIG. 1, an air conditioner design method 1 is utilized for designing an air conditioner 2 that is mass-produced. The air conditioner 2 corresponds to a vehicle air conditioner that controls an environmental condition ENV of a vehicle interior. The air conditioner 2 may additionally control an interior air volume, humidity, or the like. The air conditioner 2 controls an interior environment so that an object person feels comfortable in the interior. The object person corresponds to, for example, a driver, or an occupant of each seat. The air conditioner 2 includes a cooling cycle as a cooling device, a heating device, a controller that controls the cooling cycle and the heating device.

The comfort provided by the air conditioner 2 is provided by not only a feedback control of an interior temperature towards a target temperature but also an additional interior environment. The air conditioner design method 1 includes an evaluation stage 3 and a design stage 4. In the evaluation stage 3, the comfort of the object person is evaluated by experiments in a number of different environmental conditions ENV. In the design stage 4, a specification of the air conditioner 2 is adjusted based on a relation between an index obtained in the evaluation stage 3 and the warm sensation (degree of comfort). The air conditioner design method 1 corresponds to also a manufacturing method for manufacturing a number of the air conditioners 2.

In the evaluation stage 3, a warm sensation calculation apparatus 5 is utilized. The warm sensation calculation apparatus 5 performs a warm sensation calculation method. In the evaluation stage 3, a subject is placed in a number of the environmental conditions ENV, and declaration values of the comfort felt by the subject are collected. Simultaneously, the warm sensation calculation apparatus 5 calculates the human warm sensation as an objective index. The index indicating the warm sensation is mathematically calculated based on the environmental conditions and a human body heat model MDL. This index may be called a basic index. The basic index can include the warm sensation of the whole of the human body, the warm sensation of a part of the human body, or both.

A standard new effective temperature SET* is utilized as the basic index. The warm sensation calculation apparatus 5 calculates the SET*. The SET* is a numerical value calculated by a theoretical model (human body heat model) in which relative humidity of a standard environment is set to 50% and further human physiology response is considered by dividing the human body to which a clothing amount and a basal metabolic rate are added, into two layers of an internal layer and an external layer. The SET* is calculated based on the human body heat model MDL that simulates the human body. The SET* is calculated on an assumption that the human body heat model MDL is placed in the same environmental condition ENV as the subject. The SET* is calculated for each of a number of the environmental conditions ENV.

Furthermore, the warm sensation calculation apparatus 5 calculates a new index X by correcting the basic index. The new index X may be called as a corrected index. The calculated new index X is provided to the evaluation stage 3. The correction of the basic index is executed so as to improve a degree of coincidence between the index and the warm sensation (degree of comfort) at the transition. The transition in this case includes both of a case where the environmental condition ENV changes transiently and a case where the object person moves. The transition may include either the case where the environmental condition ENV changes transiently or the case where the object person moves.

The warm sensation calculation apparatus 5 is provided by a controller such as a microcomputer or a logic array. The controller includes at least one calculation process unit (CPU) and at least one memory device as a storage medium which stores a program and data. The controller may be provided by a microcomputer that includes a computer-readable storage medium. The storage medium corresponds to a non-transitional tangible storage medium that temporarily stores a computer readable program, and, for example, corresponds to a RAM, a ROM, or a flash memory. The storage medium may correspond to a semiconductor memory, a magnetic disk, or the like. The controller may be provided by a set of computer resources linked by a computer or a data communication device. When executed by the controller, the program causes the controller to function according to the description provided herein and causes the controller to perform the method described herein. A warm sensation calculation program is executed by the controller.

In the evaluation stage 3, the declaration value of the comfort and the calculated new index X are associated with each other. Thereby, subjective comfort (warm sensation) is replaced with the index which is an objective calculated value. For example, the declaration value has a level indicating (1) a comfortable state, (2) a slightly comfortable state, (3) a normal state, (4) a slightly uncomfortable state, (5) an unpleasant state, or the like. By this association, a designer grasps subjective warm sensation (comfort) based on the index.

In the design stage 4, the designer designs the air conditioner 2 so that the index with high comfort is reproduced. The air conditioner 2 is designed not only to merely control the temperature towards the target temperature but also to change the additional interior environment. In other words, the air conditioner 2 is designed to control not only the temperature but also other environmental conditions.

The existing air conditioner 2 also implements the additional interior environment by various methods. One example of the additional interior environment is provided by a change curve of the temperature in the interior with the lapse of time. For example, so as to increase the comfort, the temperature may be fluctuated, rapid heating may be provided, or the temperature may be slowly changed intentionally. One example of the additional interior environment is provided by a change curve of wind speed in the interior with the lapse of time. One example of the additional interior environment is provided by a difference between a temperature of the wind directed to an upper body and a temperature of the wind directed to a lower body. One example of the additional interior environment is provided by a start-up time, an operation continuation time, or a stop time of an auxiliary heating instrument. The additional interior environment may be provided by other methods.

In the design stage 4, the designer sets the additional interior environment so as to increase the comfort. For example, comfort felt in a case of entering the interior at 20° C. from the exterior of 0° C. is different from comfort felt in a case of entering the interior at 20° C. from the exterior of 10° C. Most of the object persons feel sufficient warmth and obtain high comfort in the former case. By contrast, in the latter case, most of the object persons do not feel match warmth and obtain less comfort. For example, in order to increase the comfort in the latter case, it may be considered to increase the wind speed to increase stimulation. In the design stage 4, such a control in order to increase the comfort is set in the air conditioner 2.

Figure 2:
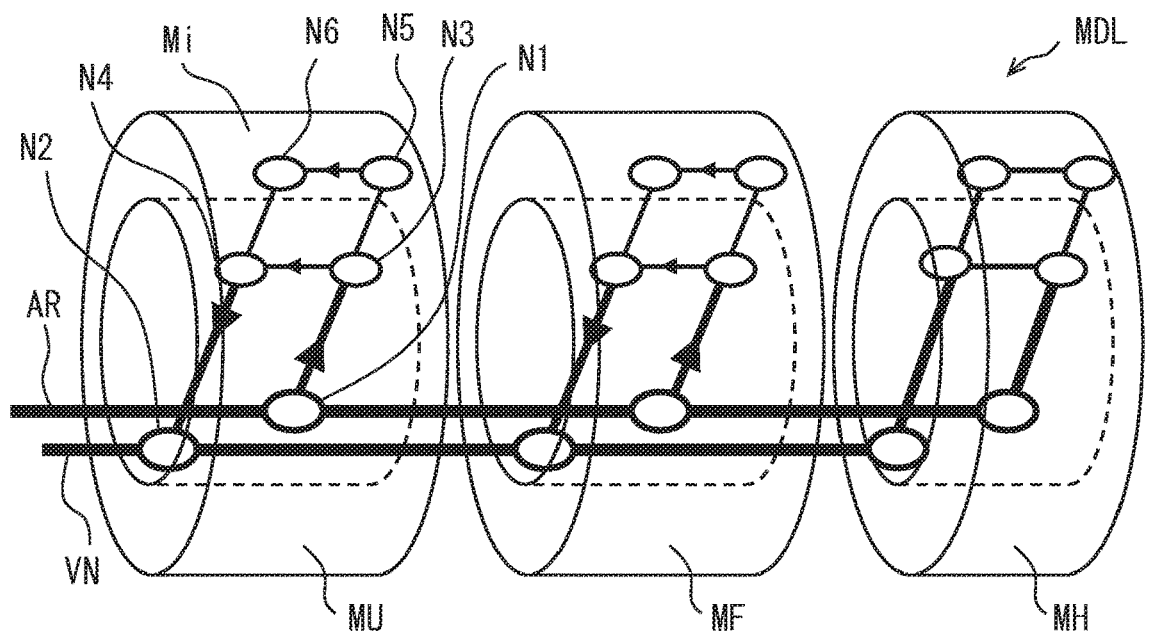
FIG. 2 is a model diagram showing a part of a human body heat model.

FIG. 2 shows one example of the human body heat model MDL. The human body heat model MDL can utilize various models. The human body heat model MDL corresponds to a function obtained by thermally modeling the human body. The human body heat model MDL includes (1) heat transfer between body tissues (including heat transfer by blood flow), (2) heat transfer between the human body and the environment where the human body is placed, and (3) body temperature adjustment response by blood flow, sweating, and metabolism.

Returning to FIG. 1, the human body heat model MDL is configured on an assumption of multiple parts Mi of the human body. It may be desirable that the human body is modeled by at least six parts such as a head, a trunk, a right arm, a left arm, a right foot, and a left foot. Further, it may be desirable to model the human body by 16 parts additionally including a neck, a chest, an abdomen, an upper arm, a forearm, a hand, a thigh, a lower leg, and a foot shown in the drawing. FIG. 1 and FIG. 2 exemplify an upper arm MU, a forearm MF, and a hand MH.

In FIG. 2, the blood flow is shown on an assumption of two systems of an arterial system and a venous system. When one part Mi of the human body is assumed, a node N1 indicating a relation between the part Mi and the artery and a node N2 indicating a relation between the part Mi and the vein may be assumable. A node N3 indicating a relation between a human inner layer at the part Mi and the artery and a node N4 indicating a relation between the human inner layer at the part Mi and the vein may be assumable. Further, a node N5 indicating a relation between a human outer layer (for example, skin) at the part Mi and the artery and a node N6 indicating a relation between the human outer layer at the part Mi and the vein may be assumable. In such a manner, the nodes are set as six blood vessel elements for one part Mi, and functionalized.

In this embodiment, the new index X indicating the warm sensation at the one part Mi of the human is calculated by reflecting heat inflow from another part and heat outflow. For example, even in a case of the end portion such as the hand MH, the heat inflow from the nearest forearm MF and the heat outflow to the nearest forearm MH may be considered. Further, indirect heat inflow and indirect heat outflow between the upper arm MU and another part may be considered. The heat inflow and the heat outflow change at the transition, and therefore are suitable for a correction element at the transition.

Figure 3:
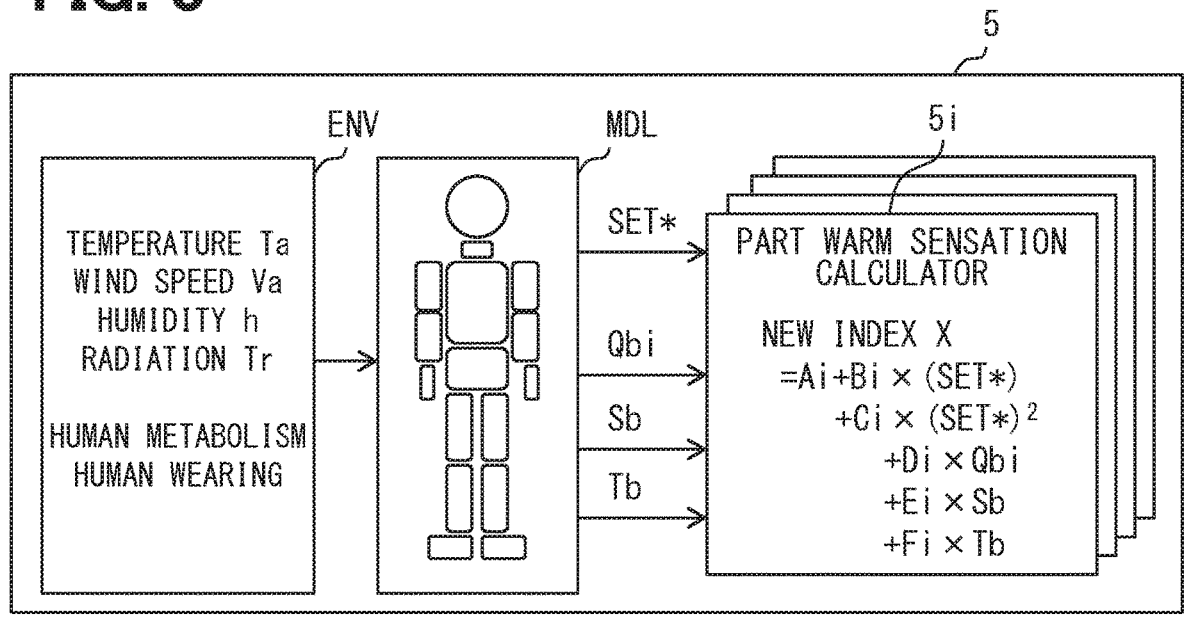
FIG. 3 is a block diagram of a warm sensation calculation apparatus.

FIG. 3 shows a block diagram of the warm sensation calculation apparatus 5. Multiple variables in an arbitrary environmental condition ENV are obtained from the human body heat model MDL. The environmental conditions ENV include temperature Ta, wind speed Va, humidity h, radiation Tr such as solar radiation in the environment where the human body is placed. These environmental conditions ENV are provided to each of the parts of the human body. For example, temperature Tai at one part Mi is provided. Thereby, for example, a difference between the temperature at the upper arm MU and the temperature at the hand MH is reflected in the warm sensation. Further, the environmental conditions ENV include the human metabolism and the human clothing. Further, the environmental conditions may include an index indicating the temperature of the seat or the variation amount of the wind speed, a heart rate, a skin temperature, an air temperature history, or the like.

The basic index of the warm sensation is obtained based on the human body heat model MDL. The human body heat model MDL provides a calculator for calculating the basic index. The basic index may correspond to, for example, the standard new effective temperature (SET*). A calculation method of the SET* is known. There is a correlation between the SET* and human warm-heat sensation. However, an error occurs in the correlation on a transient condition.

In this embodiment, the correction element for correcting the basic index is calculated. The correction element for calculating the new index X indicating the warm sensation is obtained based on the human body heat model MDL. The multiple correction elements may be utilized.

The correction elements include at least a heat transfer amount Obi due to the blood flow. The heat transfer amount Qbi due to the blood flow contributes to improving the accuracy of the index indicating the warm sensation of the human part. The heat transfer amount Qbi due to the blood flow indirectly contributes to improving the accuracy of the index indicating the warm sensation of the whole human body. The correction elements include at least a whole body heat storage amount Sb. The correction elements include at least an average body temperature Tb. The whole body heat storage amount Sb and/or the average body temperature Tb contribute to improving the accuracy of the index indicating the warm sensation of the part of the human body. The whole body heat storage amount Sb and/or the average body temperature Tb indirectly contribute to improving the accuracy of the index indicating the warm sensation of the whole of the human body.

The multiple correction elements may be desired to include the heat transfer amount Obi due to the blood flow and the whole body heat storage amount Sb or the average body temperature Tb. The multiple correction elements may be desired to include all of the heat transfer amount Obi, the whole body heat storage amount Sb, and the average body temperature Tb. The heat transfer amount Obi due to the blood flow reflects in the index, the heat transfer inside the human body due to the transient change of the environmental condition ENV. The whole body heat storage amount Sb and/or the average body temperature Tb reflects in the index, a process of increasing or decreasing the heat storage amount of the human body due to the transient change of the environmental condition ENV.

The warm sensation calculation apparatus 5 includes multiple part warm sensation calculators 5i for calculating the new index X for each of parts indicating the warm sensation of each part. One of the multiple part warm sensation calculators 5i calculates the warm sensation of the whole of the human body based on the warm sensations of the multiple parts. One of the multiple part warm sensation calculators 5i may be also referred to as a whole body warm sensation calculator. The part warm sensation calculators 5i provide a corrector that corrects the basic index. The part warm sensation calculators 5i calculate the new index X by a function of an equation (1):

$$X_i = A_i + B_i \times (SET^*) + C_i \times (SET^*)^2 + D_i \times Q_{bi} + E_i \times S_b + F_i \times T_b.$$

In this function, items from the first to the third in the right side of $(A_i + B_i \times (SET^*) + C_i \times (SET^*)^2)$ provide a basic function. The basic function corresponds to a quadratic function of the SET*. The fourth item of $(D_i \times Q_{bi})$ in the right side, the fifth item of $(E_i \times S_b)$, and the sixth item of $(F_i \times T_b)$ provide the correction amount by the correction elements. The correction elements add a direct correction component to the SET* as the basic index, and improve the degree of coincidence between the basic index and the warm sensation. The correction amount corresponds to a linear function of each correction element. The correction elements corresponds to, for example, $D_i \times Q_{bi}$, $E_i \times S_b$, or $F_i \times T_b$.

Figure 4:
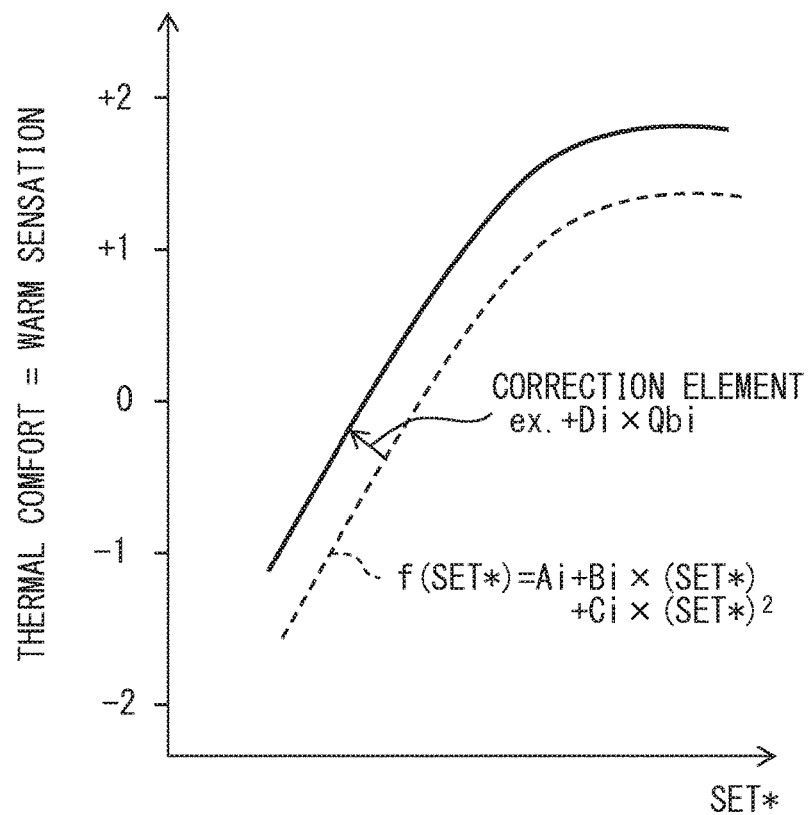
FIG. 4 is a flowchart of the warm sensation calculation apparatus.

FIG. 4 is a graph showing a relation between the SET* as the basic index and the degree of comfort. The degree of comfort may correspond to a declaration value of comfort, and also the human warm sensation. The relation between the SET* as the basic index and the degree of comfort can be represented by a basic function f (SET*). The correction amount by the component element acts as a direct component to the basic function f (SET*). For example, the fourth item of $(D_i \times Q_{bi})$ in the right side causes the basic function f (SET*) to parallelly move by adding the direct component in which the heat transfer amount Obi due to the blood flow is set as the variable. The fifth item of $(E_i \times S_b)$ in the right side causes the basic function f (SET*) to parallelly move by adding the direct component in which the whole body heat storage amount Sb is set as the variable. The sixth item of $(F_i \times T_b)$ in the right side causes the basic function f (SET*) to parallelly move by adding the direct component in which the average body temperature Tb is set as the variable. Thereby, the error at the transition is prevented. The function f (SET*) in the drawing is an example. For example, it is represented as $f(SET^*) = A_i + B_i \times (SET^*) + C_i \times (SET^*)^2$.

Figure 5:
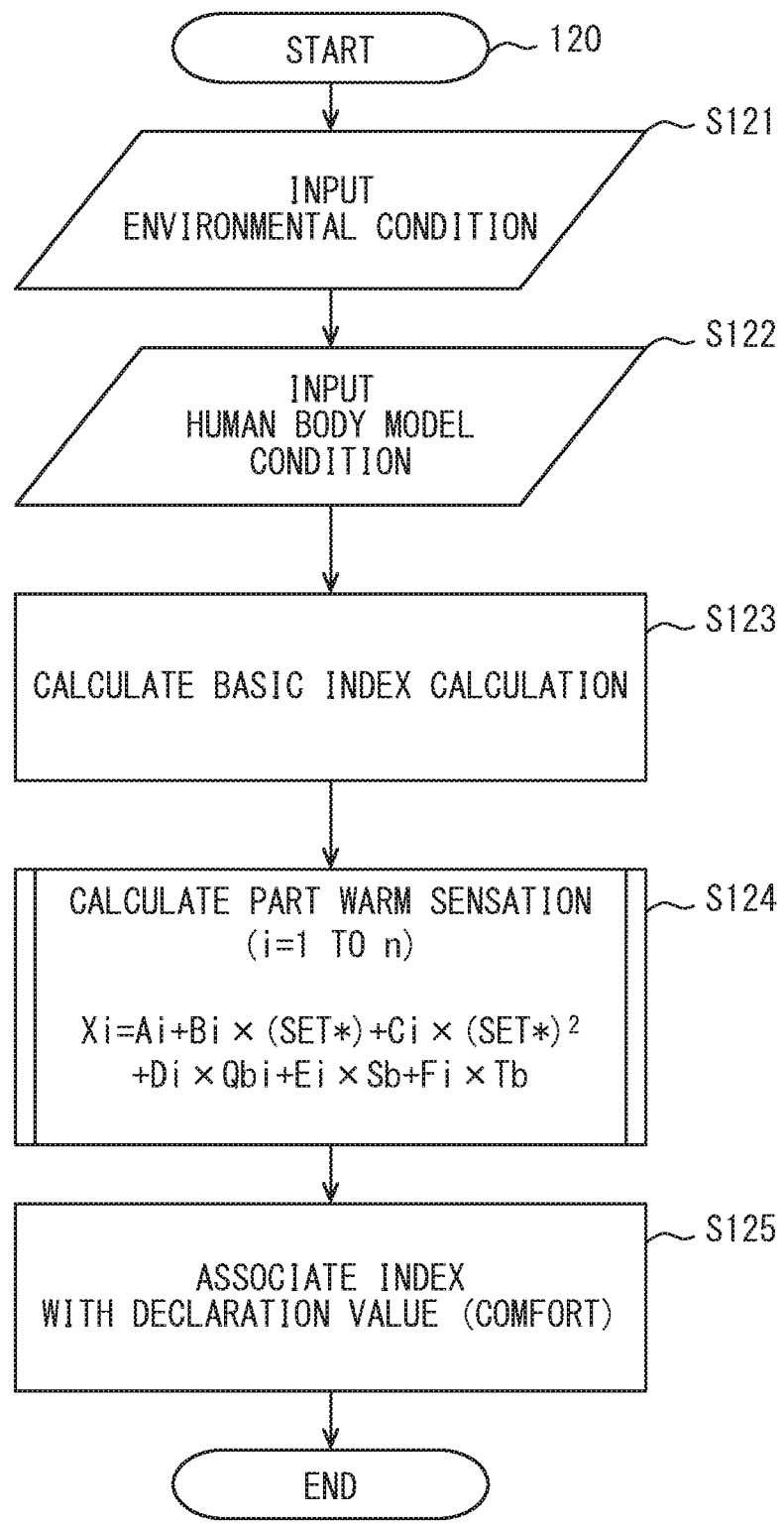
FIG. 5 is a graph showing a relation between an index indicating warm sensation and comfort.

FIG. 5 is a flowchart showing one example of a warm sensation calculation program executed by the warm sensation calculation apparatus 5. A warm sensation calculation program 120 includes S121 inputting the environmental condition ENV, and S122 inputting a condition of the human body heat model MDL. The S121 and the S122 provide an input step. As the condition of the human body heat model MDL, for example, height, weight, muscle mass, fat mass, bone mass, or the like may be employed. The condition of the human body heat model MDL may be fixed to the standard value.

The warm sensation calculation program 120 includes S123 calculating the basic index. Based on the human body heat model MDL, the SET* under the input environmental condition ENV is calculated. Further, based on the human body heat model MDL, the heat transfer amount Obi, the whole body heat storage amount Sb, and the average body temperature Tb are calculated. The S123 provides a calculation step. The S123 provides a basic calculator that calculates the basic index. The calculator corresponds to the basic calculator and the calculation step.

The warm sensation calculation program 120 includes S124 calculating the warm sensation of the whole body and the warm sensation of each part Mi. The S124 repeats the calculation for each part Mi. The S124 execute the equation (1). The SET*, the Qbi, the Sb, the Tb in the equation (1) are calculated based on the human body heat model. The Ai, the Bi, the Ci, the Di, the Ei, and the Fi are constants set for each part Mi. The S124 provides a correction step. The S124 provides a corrector that corrects the basic index. The S124 calculates the warm sensation of the human body based on the warm sensation of the multiple parts.

The S124 corrects the basic index by utilizing, as the correction element, the heat transfer amount Obi due to the blood flow of the human body heat model MDL. The S124 corrects the basic index based on the heat transfer amount Obi so as to reflect the heat inflow and the heat outflow at the specific part at the transition. The S124 further corrects the basic index by utilizing, as the correction element, the whole body heat storage amount Sb due to the heat storage of the human body heat model MDL and/or the average body temperature Tb. The S124 corrects the basic index based on the whole body heat storage amount Sb and/or the average body temperature Tb so as to reflect the heat storage of the human body at the transition. The S124 adds the direct component in which the correction element is set as the variable to the basic function f (SET*) set based on the basic index.

The warm sensation calculation program 120 may include S125 associating the calculated new index X with the declaration value (comfort). A result by an execution of the S125 is provided to the design by the designer. For example, the designer evaluates the environmental condition in which the warm sensation of the subject, that is, the comfort increases, and reflects the evaluation result in the design of the air conditioner 2.

In this embodiment, a time variation of the heat as a feature of the transient environment or a spatial heat distribution are focused. It may be considered that a prediction accuracy of the warm-heat sensation by the basic index (SET*) can be improved and adaptation even in the transition state may be implemented by adding, as the correction element, a factor indicating these features of the time variation and the heat distribution. Specifically, a model simulating the living body is utilized. For taking the time variation into consideration, the amount of the heat stored at the corresponding human body part, the heat transfer amount due to the blood flow, or the heat storage amount stored inside the part may be considered. Thereby, it may be possible to improve the accuracy of the warm-heat sensation of the human body.

According to this embodiment, it may be possible to represent the human warm sensation at the transition since the heat transfer amount Obi due to the blood flow is added as the correction element. According to this embodiment, the process of increasing or decreasing the heat storage amount of the human body due to the environmental condition ENV may be considered. Therefore, it may be possible to represent the human warm sensation at the transition. Specifically, the whole body heat storage amount Sb or the average body temperature Tb improves the accuracy of the warm sensation at the transition.

Second Embodiment

This embodiment corresponds to a modification example in which the preceding embodiment is a basic embodiment. In the embodiment, the warm sensation calculation apparatus 5 that is utilizable in the evaluation stage for designing the specification (cooling device, heating device, or control characteristics of the cooling device and the heating device) of the air conditioner 2 has been described. Instead of this, the warm sensation calculation apparatus 5 may be disposed in the air conditioner 2.

Figure 6:
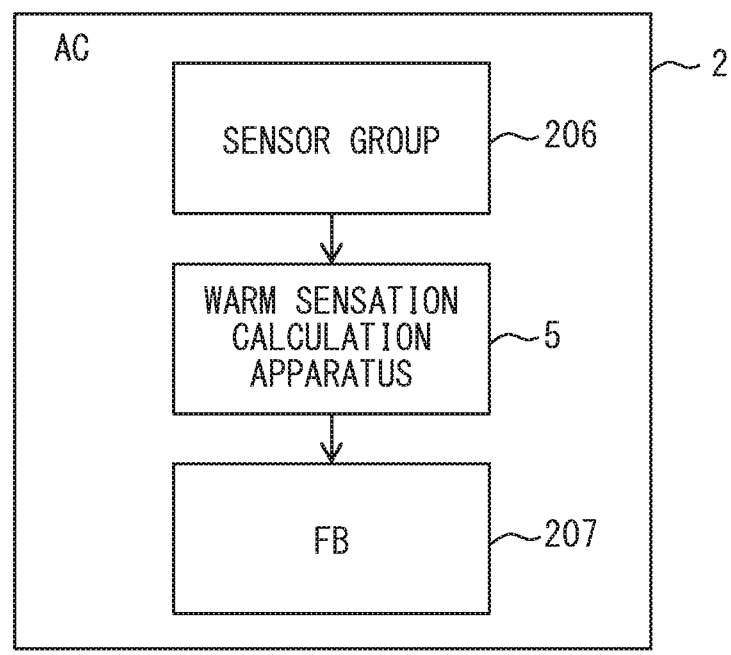
FIG. 6 is a block diagram of an air conditioner according to a second embodiment.

FIG. 6 shows the air conditioner 2 in which the warm sensation calculation apparatus 5 is disposed. The warm sensation calculation apparatus 5 inputs the interior environmental condition, and estimates the warm sensation of the object person that will be in the interior. The air conditioner 2 adjusts the environmental condition so as to improve the estimated warm sensation, that is, the calculated warm sensation (comfort). The air conditioner 2 includes a sensor group 206. The sensor group 206 detects, in real time, the interior environmental condition and the exterior environmental condition of the vehicle subjected to the air conditioning. The environmental condition detected by the sensor group 206 is input to the warm sensation calculation apparatus 5.

The warm sensation calculation apparatus 5 calculates the warm sensation (comfort) felt by the object person that will be in the vehicle interior, based on the detection information by the sensor group 206. This calculation process may also correspond to a process of estimating the warm sensation. The air conditioner 2 adjusts the environmental condition so as to improve the estimated warm sensation.

For example, the warm sensation calculated by the warm sensation calculation apparatus 5 is input to a temperature feedback controller 207 (FB). The temperature feedback controller 207 adjusts the characteristic of the feedback control based on the calculated warm sensation, in a situation where the temperature transiently changes. For example, when the temperature is changed by a predetermined temperature (for example, when the temperature is increased by 10° C.), the human warm sensation may change in accordance with the environmental condition. In such a case, the temperature feedback controller 207 performs, in accordance with the calculated warm sensation, a control in which the comfort of the subject is improved in the evaluation stage. For example, one of various changes such as (1) fast change, (2) slow change, (3) slow change after fast change, (4) fast change after slow change, and (5) change with excessive amount is selected, and the control is implemented. The temperature feedback controller 207 provides an air conditioning controller that controls the air conditioning in accordance with the new index X calculated by the warm sensation calculation apparatus 5.

According to this embodiment, it may be possible to accurately estimate the human warm sensation even at the transition. Therefore, the air conditioner capable of reflecting the human warm sensation at the transition in the air conditioning is provided.

Other Embodiments

While various embodiments, configurations, and aspects of the warm sensation calculation apparatus, the warm sensation calculation method, the air conditioner, and the program according to one aspect of the present disclosure have been exemplified, the embodiments, configurations, and aspects of the present disclosure are not limited to those described above. The disclosure encompasses the illustrated embodiments and variations based on the illustrated embodiments by those skilled in the art. For example, the disclosure is not limited to the portions and/or combinations of elements shown in the embodiments. The disclosure may be implemented in various combinations. The disclosure may have additional portions that may be added to the embodiment. The disclosure encompasses omissions of parts and/or elements of the embodiments. The disclosure includes replacements of portions and/or elements between one embodiment and another embodiment, or combinations thereof. The technical scope of the present disclosure is not limited to the description of the embodiments.

In the embodiment, the standard new effective temperature (SET*) is utilized as the basic index indicating the warm sensation. Instead of this, various indexes may be utilized. For example, an effective temperature ET, a predicted mean vote PMV, or the like may be utilized.

It is noted that a flowchart or the process of the flowchart in the present application includes multiple steps (also referred to as sections), each of which is represented, for example, as S121. Further, each step can be divided into several sub-steps while several steps can be combined into a single step.

The invention claimed is:

1. A warm sensation calculation apparatus comprising:
a calculator configured to calculate a basic index indicating a warm sensation at a part of a human body; and
a corrector configured to correct the basic index to obtain a new index Xi by utilizing, as a correction element, a heat transfer amount due to a blood flow of a human body heat model (MDL), and wherein:
the corrector corrects the basic index based on the heat transfer amount so as to reflect heat inflow and heat outflow at a transition;
the corrector further corrects the basic index by utilizing, as the correction element, a whole body heat storage amount and an average body temperature due to heat storage of the human body heat model;
the corrector corrects the basic index based on the whole body heat storage amount and the average body temperature so as to reflect the heat storage of the human body at the transition;
the correction element adds a direct correction component to the basic index to increase a degree of coincidence between the basic index and the warm sensation;
the direct correction component corresponds to a linear function of the correction element;
the corrector calculates the new index Xi indicating the warm sensation for each of parts of the human body following:

$$Xi = Ai + Bi \times (SET^*) + Ci \times (SET^*)2 + Di \times Obi + Ei \times Sb + Fi \times Tb,$$

wherein
each of Ai, Bi, Ci, Di, Ei and Fi is a constant set for each of parts of the human body,
(SET*) is the basic index,
Obi is the heat transfer amount,
Sb is the whole body heat storage amount, and
Tb is the average body temperature; and
wherein the new index is being used to affect the control of the operation of a device.

2. A warm sensation calculation apparatus comprising:
a calculator configured to calculate a basic index indicating a warm sensation at a part of a human body; and
a corrector configured to correct the basic index to obtain a new index Xi by utilizing, as a correction element, a whole body heat storage amount and an average body temperature due to heat storage of a human body heat model,
wherein:
the corrector corrects the basic index based on a heat transfer amount due to a blood flow of the human body heat model so as to reflect heat inflow and heat outflow at a transition;
the corrector corrects the basic index based on the whole body heat storage amount and the average body temperature so as to reflect the heat storage of the human body at the transition;
the correction element adds a direct correction component to the basic index to increase a degree of coincidence between the basic index and the warm sensation;
the direct correction component corresponds to a linear function of the correction element; and
the corrector calculates the new index Xi indicating the warm sensation for each of parts of the human body following:

$$Xi = Ai + Bi \times (SET^*) + Ci \times (SET^*)2 + Di \times Obi + Ei \times Sb + Fi \times Tb,$$

wherein
each of Ai, Bi, Ci, Di, Ei and Fi is a constant set for each of parts of the human body,
(SET*) is the basic index,
Obi is the heat transfer amount,
Sb is the whole body heat storage amount, and
Tb is the average body temperature; and
and wherein the new index is being used to affect the control of the operation of a device.

3. An air conditioner comprising:
the warm sensation calculation apparatus according to claim 1; and
an air conditioning controller configured to control air conditioning in accordance with the new index calculated by the warm sensation calculation apparatus.

4. A warm sensation calculation method comprising:
calculating a basic index indicating a warm sensation at a whole of a human body or a warm sensation at a part of the human body; and
correcting the basic index to obtain a new index Xi by utilizing, as a correction element, a heat transfer amount due to a blood flow of the human body heat model, a whole body heat storage amount, and an average body temperature due to heat storage of the human body,
wherein:
the correcting corrects the basic index based on the heat transfer amount so as to reflect heat inflow and heat outflow at a transition;
the correcting corrects the basic index based on the whole body heat storage amount and the average body temperature so as to reflect the heat storage of the human body at the transition;
the correction element adds a direct correction component to the basic index to increase a degree of coincidence between the basic index and the warm sensation;
the direct correction component corresponds to a linear function of the correction element;
the warm sensation calculation method further comprises calculating the new index Xi indicating the warm sensation for each of parts of the human body following:

$$Xi = Ai + Bi \times (SET^*) + Ci \times (SET^*)2 + Di \times Obi + Ei \times Sb + Fi \times Tb,$$

wherein
each of Ai, Bi, Ci, Di, Ei and Fi is a constant set for each of parts of the human body,
(SET*) is the basic index,
Obi is the heat transfer amount,
Sb is the whole body heat storage amount, and
Tb is the average body temperature; and
wherein the new index is being used to affect the control of the operation of a device.

5. A non-transitory computer-readable storage medium that stores a program for causing a computer to perform the warm sensation calculation method according to claim 4.

* * * * *